United States Patent
Dey et al.

[11] Patent Number: 5,623,810
[45] Date of Patent: Apr. 29, 1997

[54] METHOD FOR MAKING STERILE SUTURE PACKAGES

[75] Inventors: Clifford A. Dey, San Angelo, Tex.; Robert J. Cerwin, Pipersville, Pa.; J. Mark Findlay, San Angelo, Tex.; Konstantin K. Ivanov, Bound Brook, N.J.; Robert Nuñez, Asbury, N.J.; Donald Pompei, Montville, N.J.; William R. Reinhardt, Belle Mead, N.J.; Mehmet Reyhan, E. Windsor, N.J.; David A. Szabo, Branchburg, N.J.

[73] Assignee: Ethicon, Inc., Summerville, N.J.

[21] Appl. No.: 624,971

[22] Filed: Mar. 29, 1996

[51] Int. Cl.$^6$ .............................. B65B 55/02; B65B 47/00
[52] U.S. Cl. .............................. 53/425; 53/453; 53/478; 53/559; 53/281
[58] Field of Search .............................. 53/167, 281, 329.2, 53/329.3, 425, 426, 453, 478, 559

[56] References Cited

U.S. PATENT DOCUMENTS

| | | | |
|---|---|---|---|
| 2,948,999 | 8/1960 | Schlayer et al. | 53/425 X |
| 3,673,760 | 7/1972 | Canamero et al. | 53/453 X |
| 3,726,057 | 4/1973 | Kemble | 53/425 |
| 3,728,839 | 4/1973 | Glick | 53/425 |
| 3,755,042 | 8/1973 | Robertson et al. | 53/425 X |
| 3,815,315 | 6/1974 | Glick | 53/425 |
| 3,839,841 | 10/1974 | Amplatz | 53/425 |
| 4,603,538 | 8/1986 | Shave | 53/425 |
| 4,918,907 | 4/1990 | Roach et al. | 53/453 |
| 5,192,483 | 3/1993 | Kilgrow et al. | 53/453 X |
| 5,220,769 | 6/1993 | Brown et al. | 53/453 |

Primary Examiner—Daniel Moon
Attorney, Agent, or Firm—Peter J. Thoma

[57] ABSTRACT

A method for making sterile suture packages employs a frame assembly line, a sterilization line and a blanker/cartoner line. A web of foil is advanced in a series of movements through the frame assembly line to assemble a frame containing needle-suture assemblies in a plurality of cavities in the frame, the frame having top and bottom aluminum foils with heat seal coatings on their facing surfaces. The cavities are formed in the bottom foil of each frame by a combination of pressurized air and mechanical plugs which are forced against the bottom foil and an underlying die having recesses for defining the cavities. A blanking operation following sterilization and sealing separates individual packages, each containing one needle-suture assembly, from the frame. The packages are then conveyed by belts through inspection stations and reoriented for loading into shipping cartons.

6 Claims, 13 Drawing Sheets

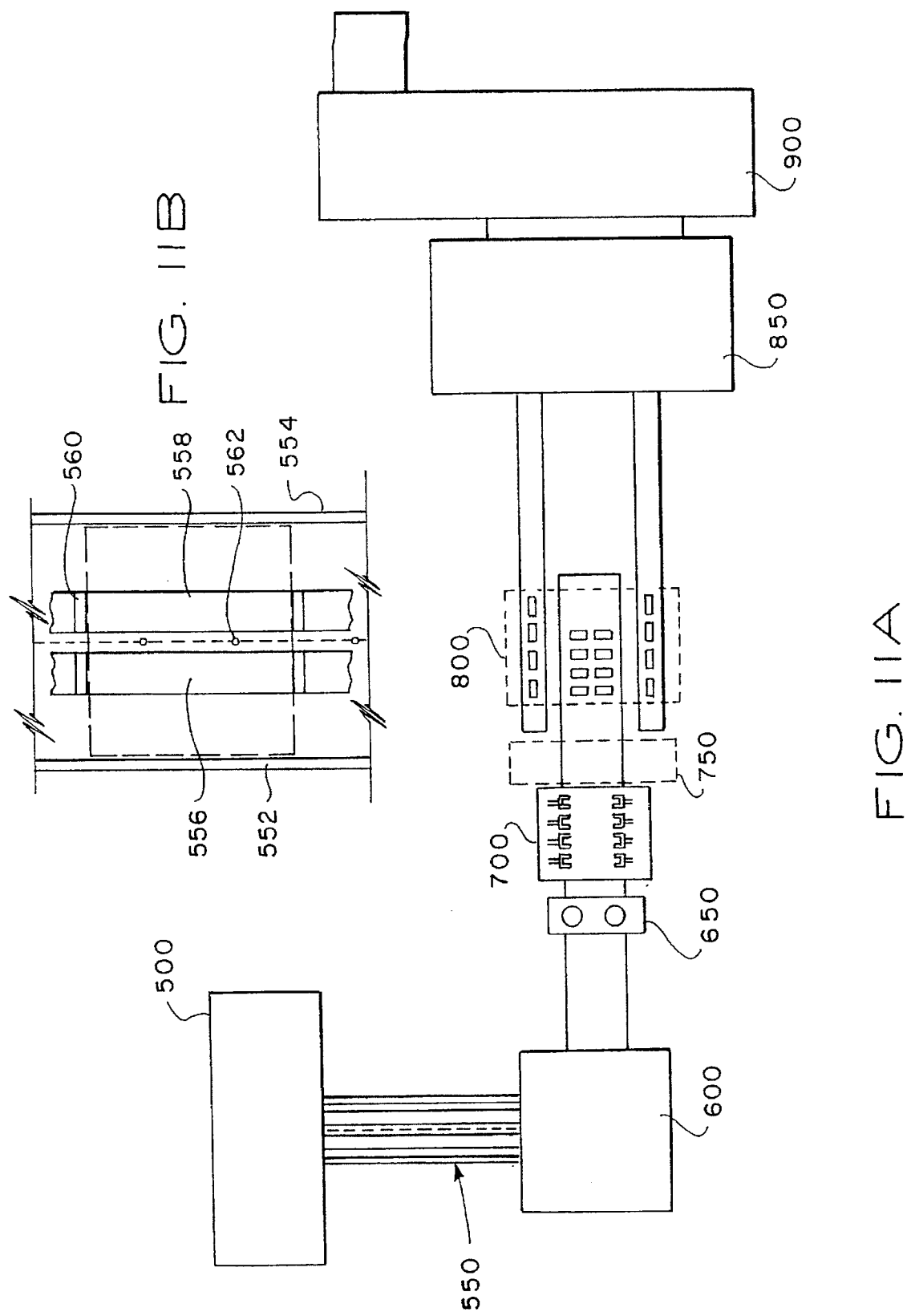

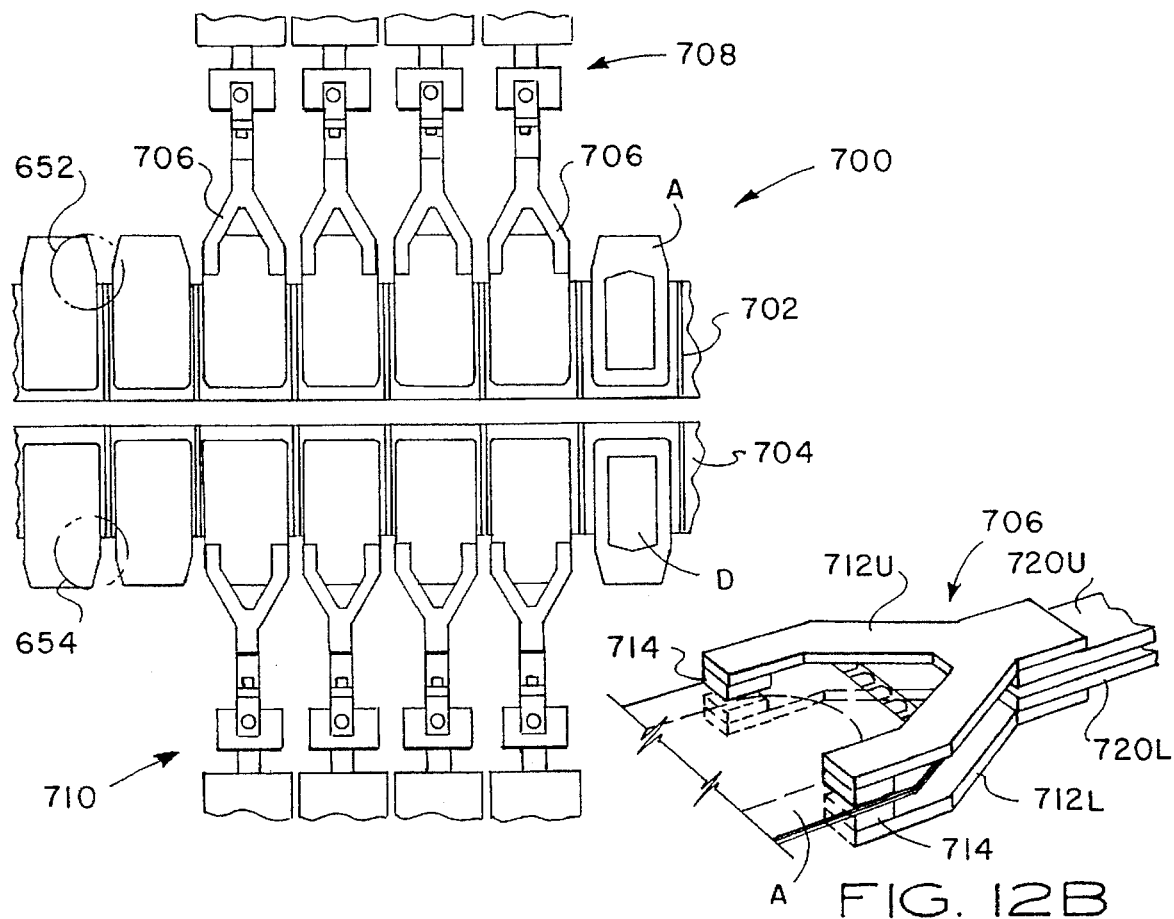
FIG. 12A
FIG. 12B
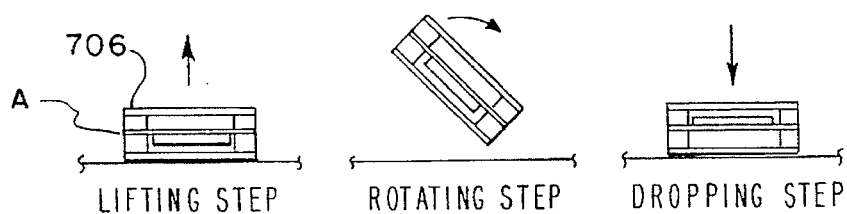
FIG. 12C 5,623,810

1

METHOD FOR MAKING STERILE SUTURE PACKAGES

CROSS-REFERENCE TO RELATED APPLICATIONS

This application is related to two commonly-assigned patent applications filed in the U.S. Patent and Trademark Office on the same day as this application, Mar. 29, 1996 the first such application being entitled "Apparatus for Feeding Foil Stock in a Process for Making Sealed Sterile Packages" Ser. No. 08/624,926 and the second such application being entitled "Improved Surgical Suture Package with Peelable Foil Heat Seal" Ser. No. 08/623,874 the disclosures of each such application being incorporated herein by reference.

BACKGROUND OF THE INVENTION

The present invention relates to methods for the manufacture of sealed sterile packages, and more particularly to automated procedures for making sealed sterile packages for surgical sutures, and readying such packages for boxing and shipment to users.

Automated manufacturing procedures for packaging sterile surgical suture products require sophisticated equipment that executes a series of operations on packaging material as it moves from station to station down line through the equipment. The efficient operation of the equipment requires precise timing and control of components of the equipment at critical stations along the manufacturing line. The present invention describes improvements in the methods and systems for manufacturing sealed sterile packages for surgical sutures.

SUMMARY OF THE INVENTION

In accordance with the present invention, automated procedures are employed to package surgical suture products in a sterile condition for shipment and subsequent use in surgery. As part of the packaging procedure, needle-suture assemblies are retained in a packet comprising a plastic tray and a paper lid. The needle-suture assembly comprises a pointed needle with a long strand of suture material attached to the blunt end of the needle. The needle is held in place in the tray by resilient slotted ribs, and the suture is retained in a coiled arrangement in a track at the periphery of the tray. The paper lid covers a portion of the tray leaving at least the blunt end of the needle exposed for access with forceps during surgery.

The packet containing the needle-suture assembly is sealed between two metal foils that comprise a sterile package, which is subsequently opened in the operating room. The sterile package has a cavity within which the suture packet resides. A seal is formed around the cavity by pressing the two foils together using a heated die mechanism which melts thin polymer coatings on the facing surfaces of the foils in the area exposed to the heated die. Unsealed flaps at the end of the package facilitate peeling open the package in the operating room.

The packages are processed through packaging equipment in groups which define a frame. The groups of packages move from station to station through packaging and sterilization equipment in a controlled manner. Preparation, sterilization and final packaging of sealed foil packages occur on three consecutive manufacturing lines consisting of a frame assembly line, a sterilization line and a blanker-cartoner line.

In accordance with the present invention, improved packaging methods performed in a controlled sequence of operations as described herein enable efficient manufacturing of sterile surgical suture packages. The presently preferred way of carrying out the invention is described in detail below with reference to the accompanying drawings.

BRIEF DESCRIPTION OF THE DRAWINGS

FIG. 11A is a top schematic view of a layout for a blanker-cartoner line;

FIG. 11B is an enlarged view of a portion of a feed line for transporting frames of packages to a blanking station in the blanker-cartoner line;

FIG. 12A is a schematic top view of a flipper station in the blanker/cartoner line in which a set of eight sealed suture packages are about to be rotated 180° to permit visual inspection of their bottom surfaces;

FIG. 12B is a schematic perspective view of a flipper yoke engaging the edges of a package at points in the seal area as a first step in the flipping sequence;

FIG. 12C schematically illustrates three end views of a package grasped by a flipper and being carried through a lifting step, a rotating step and a dropping step at a single position in the flipper station of FIG. 12A;

DETAILED DESCRIPTION OF THE INVENTION

Figure 1:
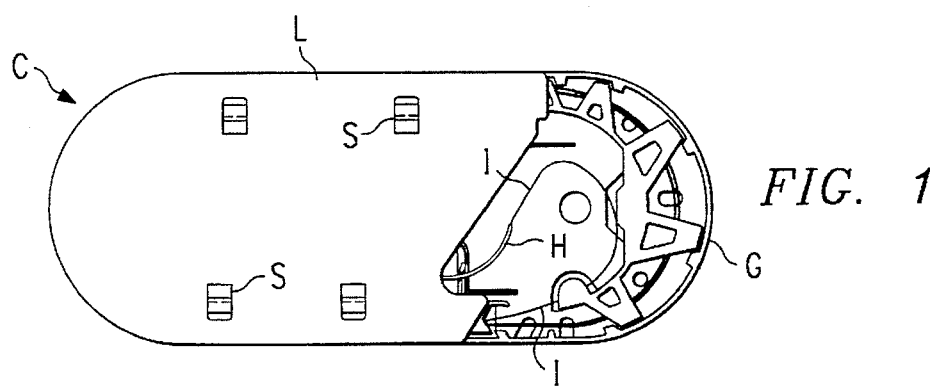
FIG. 1 is a top plan view of a suture packet, which is packaged in accordance with the present invention.

Referring to FIG. 1, a surgical suture packet preferably employed in the procedure of the present invention is illustrated and designated generally by reference letter C. The packet C comprises an oval-shaped plastic tray G, a major portion of which is covered by a stiff paper lid L. The tray G retains a needle-suture assembly consisting of a needle H and a suture I. The suture I is attached to the blunt end of the needle H in a well known manner, such as by insertion of the end of the suture into an opening or channel in the end of the needle, and then crimping or swaging the end of the needle to tightly secure the suture thereto. The tray G has a peripheral track which retains an extended length of suture therein in a coiled arrangement. The needle H is resiliently held in place by slotted ribs integrally formed in the base of the tray G. The lid L is held in place by depressing portions of the paper into sockets S. The preferred suture packet C is described more fully in the aforementioned co-pending patent application entitled "Improved Surgical Suture Package with Peelable Foil Heat Seal."

Figure 2:
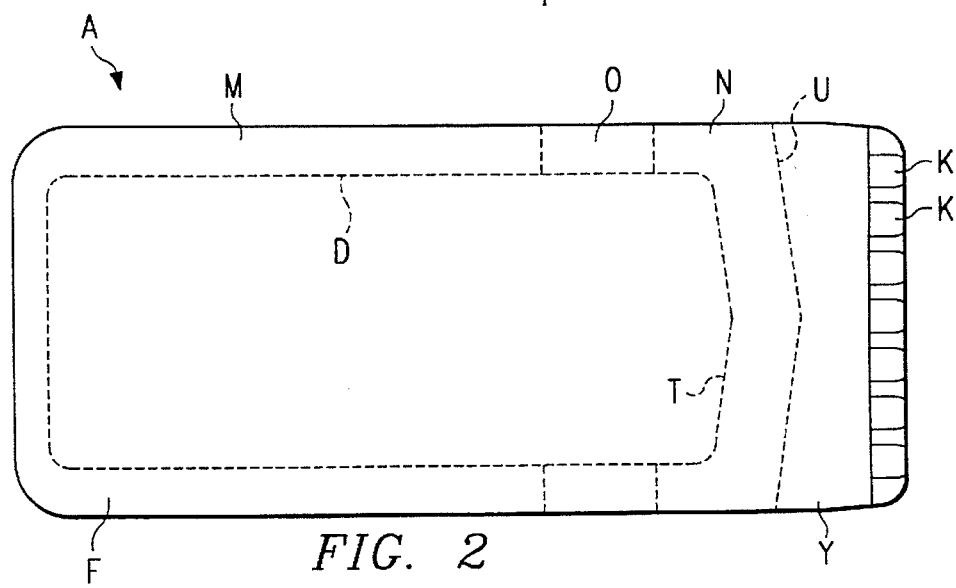
FIG. 2 is a top plan view of a sealed surgical suture package manufactured in accordance with the present invention.
Figure 3:
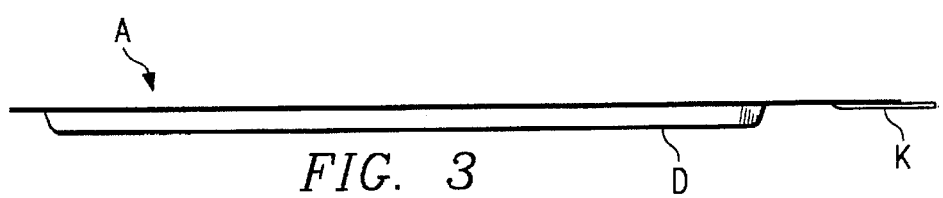
FIG. 3 is a side view of the package of FIG. 2.
Figure 4:
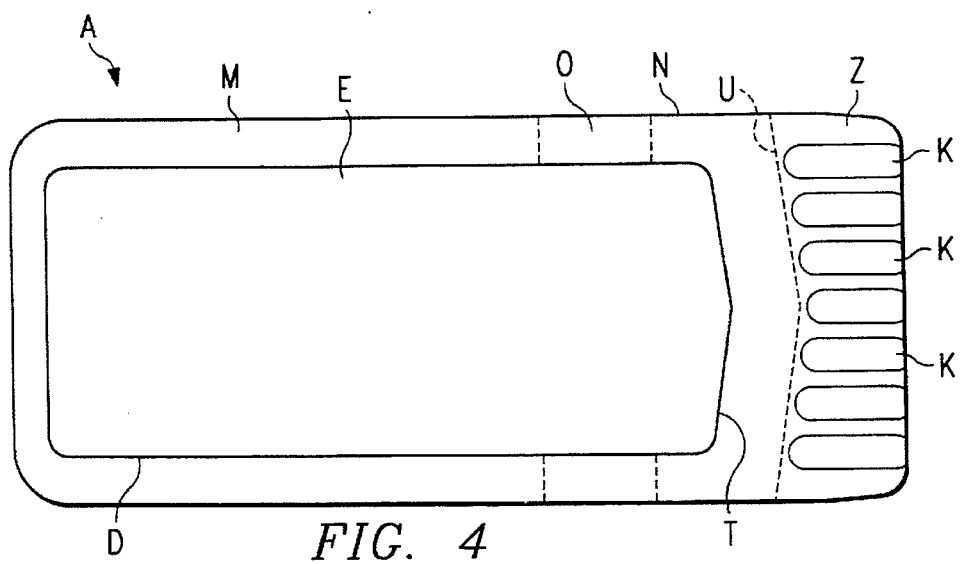
FIG. 4 is a bottom view of the package of FIG. 2.

Now referring to FIGS. 2–4, a preferred package formed in accordance with the present invention will be described. The package is designated generally by reference letter A and comprises peelable metal foils which retain the suture packet C in a cavity therein in a sterile condition. The bottom foil E has an elongated cavity D shaped to accommodate the suture packet C. A top foil F is placed on the bottom foil E after the packet C has been loaded into the cavity D. The foils E and F are preferably aluminum foils having thin polymer coatings on their facing surfaces which permit the formation of a heat seal around the periphery of the cavity D.

Unsealed flaps are provided at the front end of the package A to facilitate peeling open the package to access the suture packet C in the operating room. The top foil F includes a flap Y and the bottom foil E includes a flap Z, the flap Z extending beyond the flap Y to facilitate separation of the flaps with one's fingers. The bottom flap Z includes rib-like depressions K which add stiffness to the bottom flap to resist crumpling during handling.

In the packaging procedure, the cavity D is formed in the bottom foil E, the suture packet C is loaded into the cavity D, a primary seal M is formed along the back end and part way along the two sides of the cavity D, the package A is subjected to a sterilization procedure, a secondary seal N is formed around the front end of the cavity D in an overlapping relationship with the primary seal M, and the package A is processed further for loading into cartons for shipment to the customer. The primary seal M and secondary seal N overlap in a portion of the peripheral seal indicated by the letter O.

The cavity preferably has an apex-shaped front edge T. The portion of the seal N between the front edge T of the cavity D and the ribs K is preferably chevron-shaped terminating in an apex-shaped leading edge U. Further details of the preferred package A are described in the aforementioned co-pending patent application entitled "Improved Surgical Suture Package with Peelable Foil Heat Seal."

Figure 5:
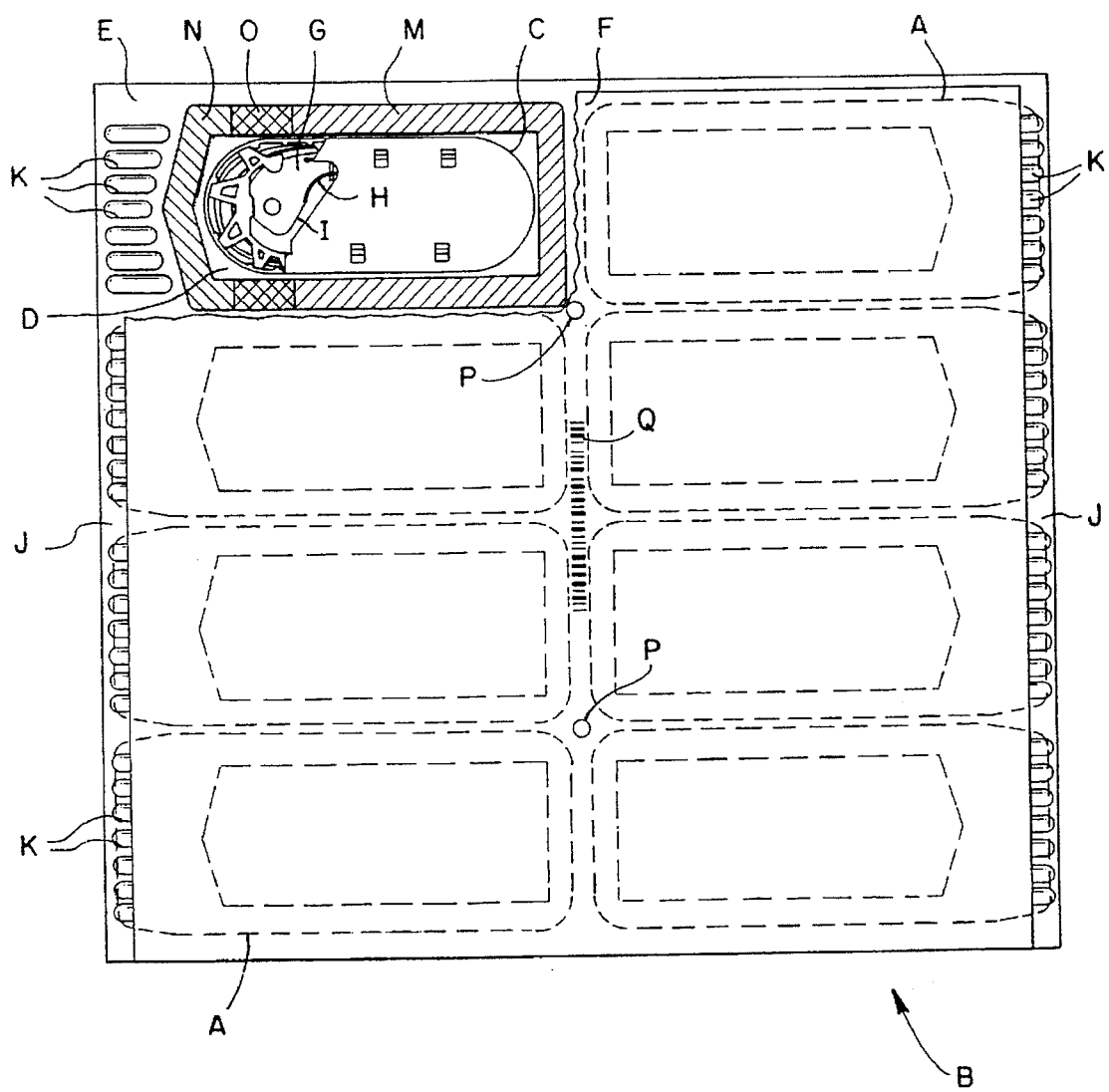
FIG. 5 is a top plan view of a frame of eight surgical suture packages of the present invention at an intermediate stage in the manufacturing procedure.

Now referring to FIG. 5, a frame of eight packages A, arranged in two rows of four packages per row, is illustrated and designated generally by reference letter B. The frame B is shown at a stage in the manufacturing process following sterilization and sealing. The subsequent steps include a blanking operation, in which the individual packages A are separated from the frame B, followed by final package inspection and boxing in cannons for shipment to the customer.

The top foil F of the frame B is shown broken away in the upper left-hand corner to reveal one suture packet C lying in a cavity D. The locations of the primary seal M and secondary seal N are shown cross-hatched with the overlap portion O double-cross-hatched. In the preferred method, the ribs K are formed simultaneously with the formation of the depressions which define the cavities D. There are preferably seven elongated ribs K per cavity D oriented as shown. The ribs K extend into an area of the bottom foil E which defines an outer flange J along each side of the frame B extending beyond the sides of the top foil F. Along the centerline in the direction of travel of the frame through the packaging equipment are disposed two locating holes P, which facilitate registration of the frame B as it moves from station to station in the manufacturing procedure. In the blanking operation, the portion of the frame B around the dashed outlines of each of the packages A is cut away to provide separate packages. The portion of frame B that is cut away in the blanking operation is scrapped. A bar code Q may also be provided in the scrap area between the locating holes P for product and lot identification during the frame assembly and sterilization procedures.

In the preferred manufacturing procedure, a roll of foil stock is provided at the front end of the frame assembly line. The foil stock is fed as a continuous web through a series of stations using improved packaging equipment as described in more detail in the aforementioned co-pending patent application entitled "Apparatus for Feeding Foil Stock in a Process for Making Sealed Sterile Packages."

Figure 6A:
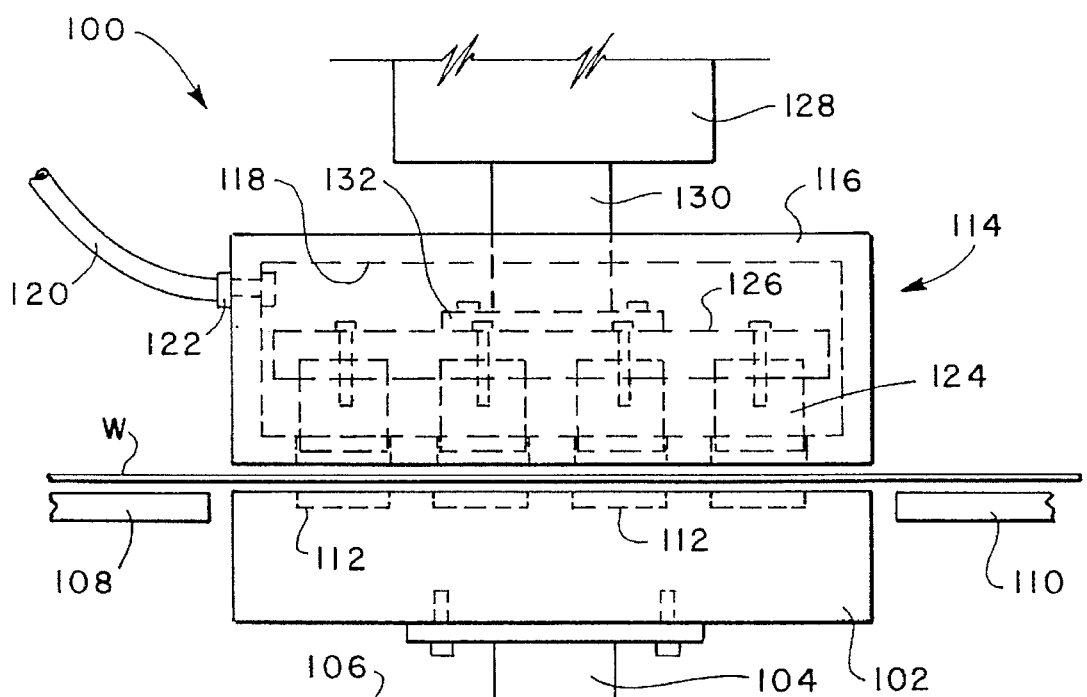
FIG. 6A is a schematic cross section at a station in a frame assembly line showing a cavity-forming die mechanism with a web of foil stock passing therethrough with the die mechanism in an open position.
Figure 6B:
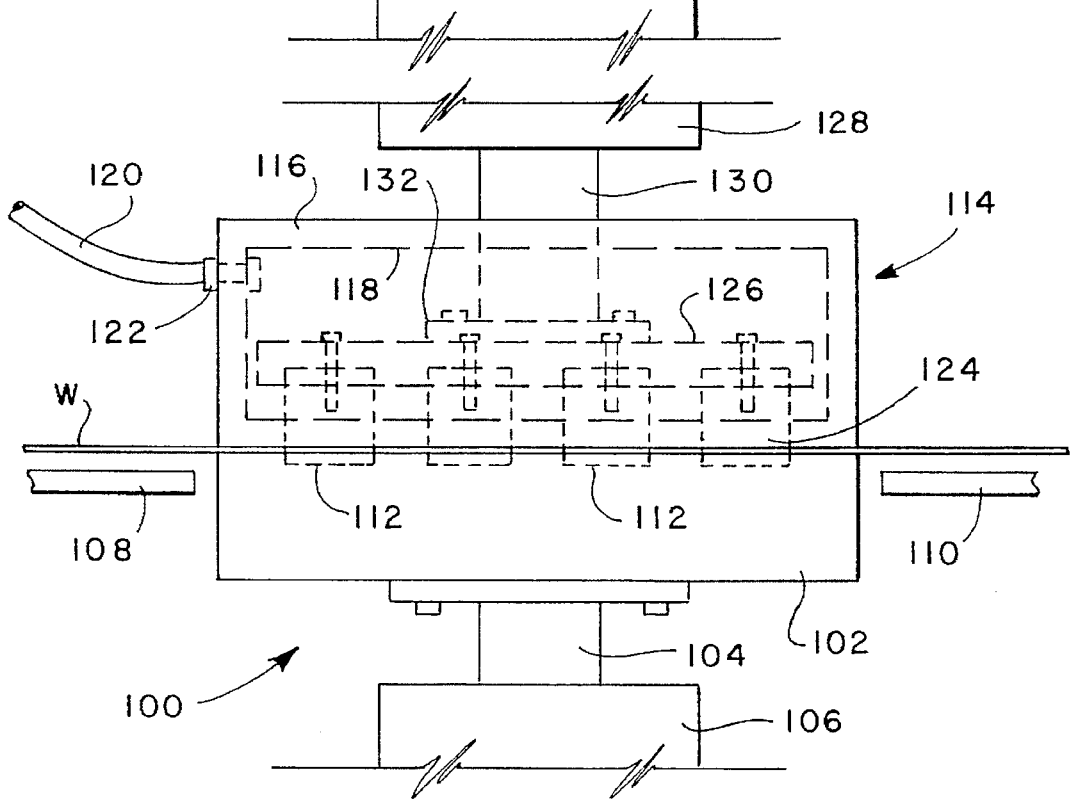
FIG. 6B is a schematic cross section similar to FIG. 6A but with the die mechanism in a closed position.
Figure 6C:
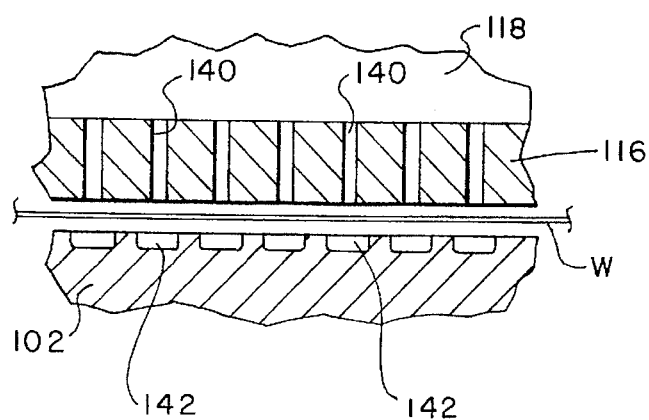
FIG. 6C is an enlarged cross section of a portion of the die mechanism of FIG. 6A schematically depicting the web between elements for forming rib-like depressions in the web.

Referring now to FIGS. 6A and 6B, a cavity-forming station is illustrated schematically and designated generally by reference 100. The web of foil stock is designated by reference letter W and is seen in edge view moving through the cavity-forming station 100. A lower die 102 is mounted on a ram 104 of a lower hydraulic press 106, which in turn is mounted on the manufacturing floor (not shown) beneath the web W. Guide platforms 108 and 110 are provided at the upstream and downstream ends of the station 100 to support and guide the web W upon entering and leaving the station 100. The lower die 102 has eight large recesses 112 (four of which are depicted in dashed outline) and 56 small recesses (seven of which are depicted in FIG. 6C).

Figure 6D:
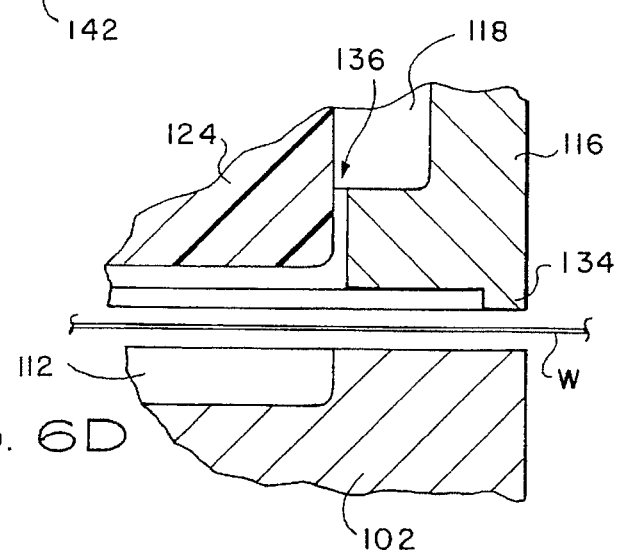
FIG. 6D is an enlarged cross section of a portion of the die mechanism of FIG. 6A schematically depicting elements for forming one of the cavities in the web.
Figure 6E:
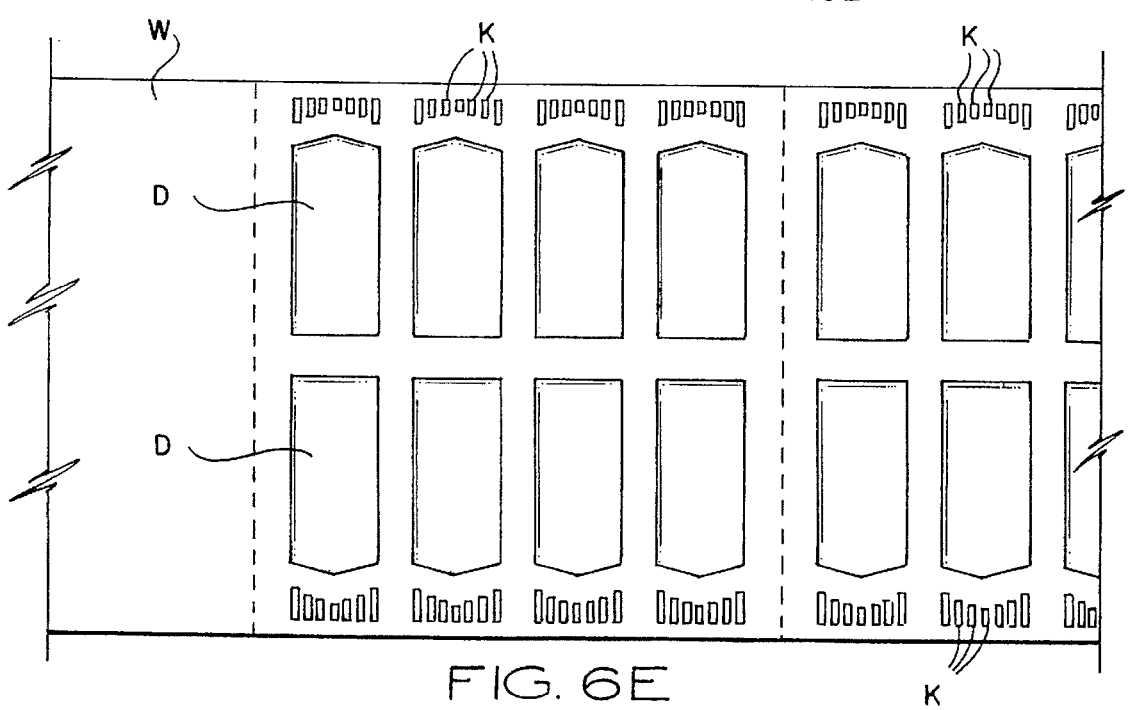
FIG. 6E is a top plan view of the web just after the cavities and rib-like depressions have been formed therein by the die mechanism in the step depicted in FIG. 6B.

Referring briefly to FIG. 6E, the web W is shown with one frame section between the dashed lines after it has had cavities D formed therein at the cavity-forming station 100. The pattern of cavities D conforms to the pattern of large recesses 112 in the lower die 102. The pattern of rib-like depressions K in each frame conforms to the pattern of 56 small recesses in the lower die 102.

Referring again to FIGS. 6A and 6B, an upper die mechanism is designated generally by reference 114. The mechanism 114 comprises a stationary plenum 116 having an interior chamber 118 shown in dashed outline. A high pressure pneumatic tube 120 for providing pressurized air to the plenum chamber 118 is secured to one wall of the plenum 116 by fittings 122. Eight cavity-forming plugs 124 (four being shown in dashed outline), are provided in the upper die mechanism 114 in position to move through openings in the bottom wall of the plenum 116. The plugs 124 are mounted to the underside of a common plate 126. A hydraulic press 128 disposed above the plenum 116 has an extendable ram 130, which passes through the top wall of the plenum 116 and is connected to the plate 126 by means of a flange 132 secured to the end of the ram 130. The ram 130 forms an air-tight seal with the portion of the top wall of the plenum 116 through which the ram 130 passes, so that a relatively high pressure can be maintained within the plenum chamber 118.

In operation, the web W is advanced to bring a frame section into position at the cavity-forming station 100. One frame section is indicated by the portion of the web W between the dashed lines in FIG. 6E. The web W moves through the cavity-forming station when the dies are in the retracted position shown in FIG. 6A. Then, the lower die 102 is raised against the underside of the web W to meet the plenum 116 as shown in FIG. 6B.

As seen in the enlarged view of FIG. 6D, an air-tight seal is formed by a downwardly extended collar 134 at the periphery of the plenum 116 contacting the periphery of one frame section of the web W and pushing it (in the closed position) against the top surface of the lower die 102. A small space 136 exists between the vertical edges of each of the plugs 124 and the adjacent edges of the lower wall of the plenum 116. These small spaces 136 permit air under high pressure to be directed at the web W in the outline of the cavities D and the correspondingly shaped recesses 112 in the lower die 102.

Referring to FIG. 6C, 56 small passageways or nozzles 140 are provided in the lower wall of the plenum 116, each nozzle being positioned immediately above a corresponding small recess 142 in the lower die 102. The recesses 142 conform in shape and location to the shapes and locations of the rib-like depressions K of each frame section as shown in FIG. 6E. The nozzles 140 communicate with the plenum chamber 118 so that pressurized air can be applied therethrough to the web W at the points above the recesses 142.

After the die 102 and plenum 116 are in sealing contact with the web W, a blast of high pressure air is injected into the plenum chamber 118 through the tube 120. This blast of air provides an initial deformation of the web W in the outline of the large recesses 112. Then, a fraction of a second later, the press 128 strokes the ram 130 downward forcing the plugs 124 into the recesses 112 of the lower die 102 to complete the process of deforming the web W in the shape of the recesses 112 to define the cavities D. The force of the air pressure through the nozzles 140 is sufficient to deform the web W in the corresponding small recesses 142 in the lower die 102 without assistance by the press 128.

After the cavities D and rib-like depressions K have been formed in the foregoing manner, the high pressure air source (not shown) connected to the tube 120 is shut off from communication with the plenum chamber 118, and the plugs 124 are raised away from the web W while the lower die 102 is being retracted to complete the forming cycle. This returns the station 100 to the open position shown in FIG. 6A. The web W is then advanced one frame section to bring a new unformed portion into the cavity-forming station 100. This completes the cycle of operation of the cavity-forming station 100.

Figure 7A:
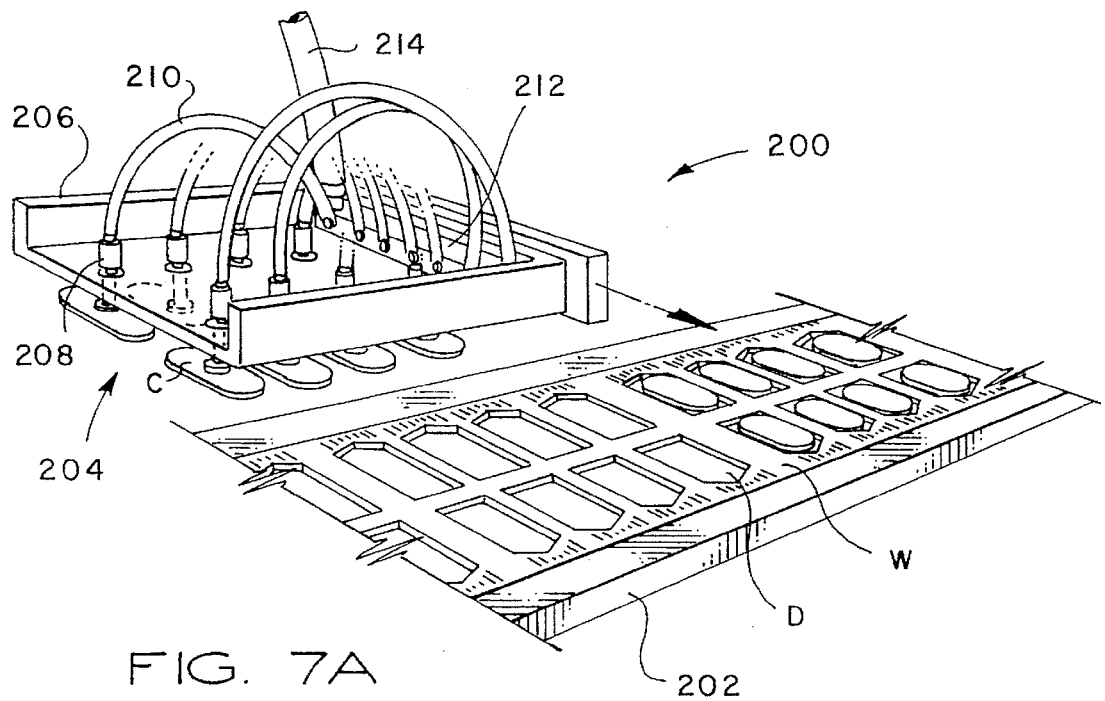
FIG. 7A is a schematic perspective view at a packet loading station in the frame assembly line showing a packet loading mechanism in a first position after having picked up a set of eight packets.
Figure 7B:
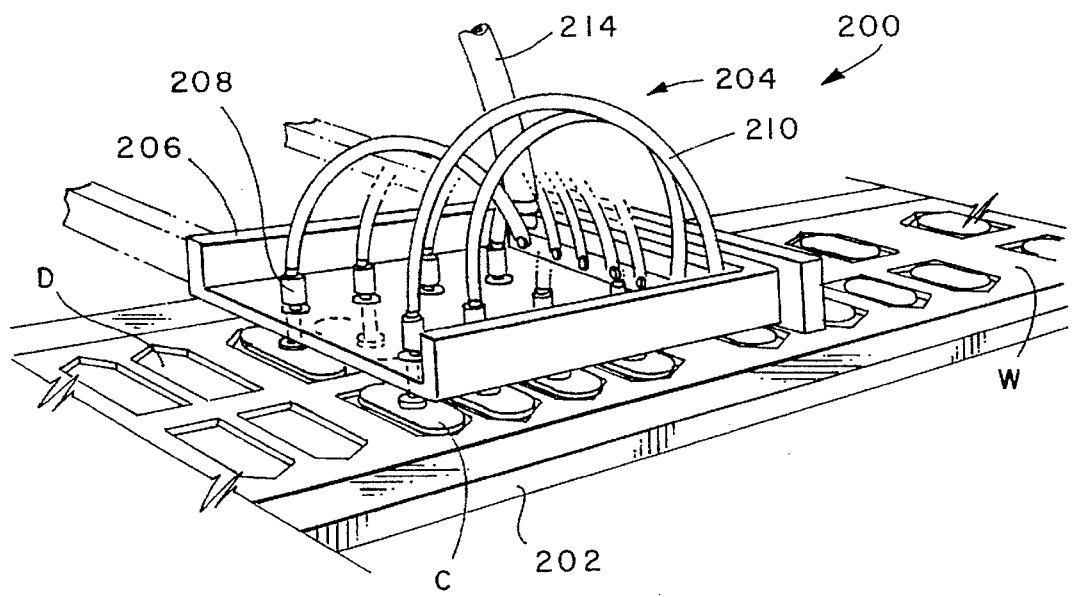
FIG. 7B is a schematic perspective view similar to FIG. 7A with the packet loading mechanism in a second position dropping eight packets into cavities in the web as it pauses at the packet loading station during the web's movement along the frame assembly line.

Now referring to FIGS. 7A and 7B, a packet loading station is illustrated and designated generally by reference 200. The web W of foil moves through the station 200 along the surface of a guide track 202. In FIG. 7A a packet loading mechanism, designated generally by reference 204, is shown in the pickup position after having just picked eight suture packets C from a feed line (not shown) adjacent to the guide track 202 of the frame assembly line. The packet loading mechanism 204 has a carriage 206 to which eight vacuum pickup heads 208 are secured with their ends extending below the surface of the carriage 206 in position to access a set of eight suture packets. The vacuum pickup heads 208 are connected by hoses 210 to a common manifold 212 located along one side of the carriage 206. The manifold 212 pneumatically communicates with an airline 214 which is connected to a vacuum pump (not shown). The packet loading mechanism 204 includes means (not shown) for raising and lowering the carriage 206, as well as moving it horizontally back and forth between the feed line and the web travel line, as will be appreciated from the description of the operation which follows. Various means for controllably moving the carriage 206 in such manner are known in the art and may be used to carry out the method of the present invention.

With particular reference now to FIG. 7B, the packet loading mechanism 204 is shown with the carriage 206 extended horizontally to a packet placement position over the web W in station 200. The carriage 206 is also shown in its lowered position ready to drop a set of eight packets C into a corresponding set of eight cavities D in one frame section of the web W. This is accomplished by releasing the vacuum in the hoses 210 under the automatic synchronized operation of the vacuum pump system (not shown).

The operation of the packet loading mechanism 204 is as follows. The web W is moved along the frame assembly line atop the guide track 202 through the packet loading station 200 in cycles, each cycle including a dwell phase and a web advancement phase. Naturally, synchronization of the web advancement system and the cycle of movement of the packet loading mechanism 204 is essential. During the time when the web W is moving in the web advancement phase, the carriage 206 can also be moving. The carriage 206 proceeds to pick up a set of eight packets C from the feed line (not shown) as depicted in FIG. 7A and move them out over the frame assembly line as depicted in FIG. 7B. The web W must be stopped in the dwell phase of its cycle when the packets C are released by the vacuum pickup heads 208 with the carriage 206 in the position shown in FIG. 7B. Then, the carriage 206 can be raised vertically and retracted horizontally to fetch an additional set of eight packets C as the web W is advanced one frame section in the direction from left to right in FIG. 7A. This completes the packet loading operation.

Figure 8A:
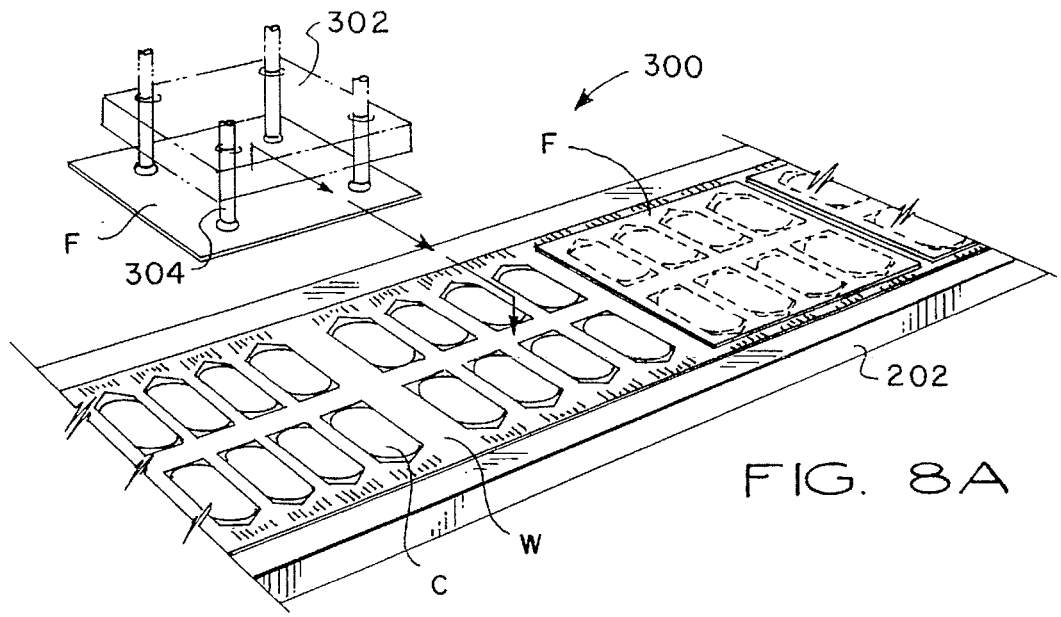
FIG. 8A is a schematic perspective view at a top foil loading station in the frame assembly line showing a top foil loading mechanism in a first position after having picked up a sheet of foil in preparation for placing it on the web of bottom foil.
Figure 8B:
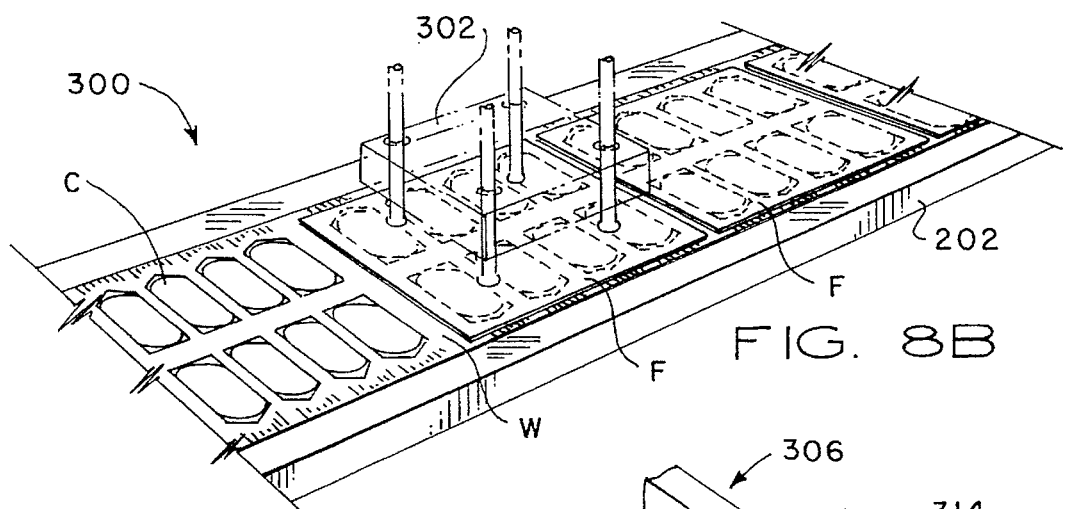
FIG. 8B is a schematic perspective view similar to FIG. 8A with the top foil loading mechanism foil shown in phantom in a second position just after having placed the sheet of top foil on the web of bottom foil.

Now referring to FIGS. 8A and 8B, a top foil loading station is illustrated and designated generally by reference 300. Sheets of top foil F are shown being loaded on frame sections of the web W, each frame section including a set of eight suture packets C, the packets having been loaded therein at station 200 as just described. The sheets of top foil F are picked up from a stack (not shown) to one side of the frame assembly line. FIG. 8A shows a pickup plate 302 in phantom outline with four vacuum pickup heads 304 mounted therein in position to access a sheet of top foil F. The plate and vacuum pickup heads then move the sheet of foil F out over the web W at station 300. Then the plate 302 is brought down to the position shown in FIG. 8B to place a sheet of foil F atop a frame section of the web W to cover eight suture packets as shown.

A conventional mechanism (not shown) is used for moving the plate 302 through the sequence of steps of picking up a sheet of foil, moving it out over station 300, lowering the foil sheet, and then returning up, horizontally back and down to the foil stack (not shown). Those skilled in the art will understand how to implement such a mechanism as a means for carrying out the method of the present invention.

Figure 8C:
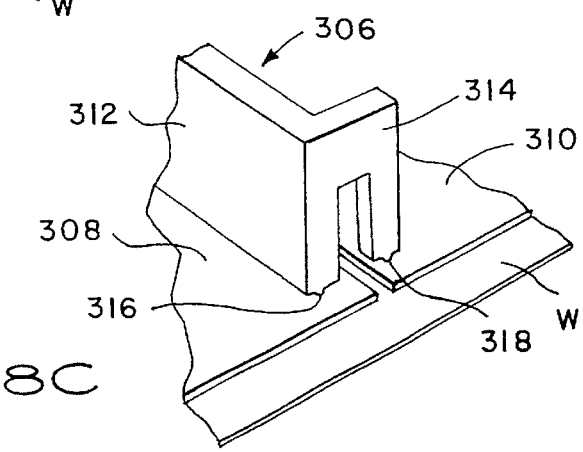
FIG. 8C is a schematic perspective view of an edge portion of the web of bottom foil and adjacent corners of top foil with a tacking iron shown in part and in contact with the adjacent corners of top foil.

Now referring to FIG. 8C, a technique for holding the sheets of foil F in place relative to the web W as the web moves will be described. By way of example, a tacking iron 306 is shown contacting two edges of adjacent sheets 308 and 310 of top foil. Top foil sheet 310 is one frame position downstream from top foil sheet 308. The tacking iron 306 is shown in part and includes a transverse beam 312 extending across the web W above the leading edge of the sheet of top foil 308, which has just been placed on the line and is still being held by the vacuum pick up heads 304 (FIG. 8B). The tacking iron 306 also includes longitudinally oriented extensions, only one of which is explicitly illustrated in FIG. 8C and designated by reference numeral 314. The unillustrated extension is at the other end of the beam 312 extending in like manner as the extension 314 over a corner of the sheet of foil 310. The beam 312 has on its bottom surface a narrow bar 316 which is coextensive with the beam. The extension 314 has a pointed tip 318 on its bottom surface, a similar tip being provided on the bottom of the unillustrated extension at the opposite end of the beam 312.

The tacking iron 306 is heated sufficiently to melt the polymer coatings on the facing surfaces of the web W and top foil sheets 308 and 310. These polymer coatings are fused at the points of contact between the iron and the sheets of top foil. This tacking operation is performed just after a sheet of foil has been lowered into position as shown in FIG. 8B. The tacking iron 306 is then swung down quickly to contact the adjacent sheets of foil 308 and 310. The tip 318 contacts one corner of the sheet of foil 310 at its trailing edge, a similar point contact being made at the other trailing edge corner of foil sheet 310. The bar 316 contacts the foil sheet 308 along a line extending along most of the leading edge of the sheet 308. A hard rubber tacking strip (not shown) lies under the web W to force the web and sheets of top foil together under the opposing force of the tacking iron 306. The spots of seal coating fused at the corners of the trailing edges of the sheets of foil are typically less than 0.250 inch in diameter and preferably are about 0.125 inch in diameter. The line of fused seal coatings produced along the leading edge of foil sheet 308 is preferably about 0.125 inch in width. The fused spots and fused line of seal coatings produced by the tacking iron 306 are located in the scrap area of the frame, which is later cut away in the blanking operation, as described below.

Figure 9A:
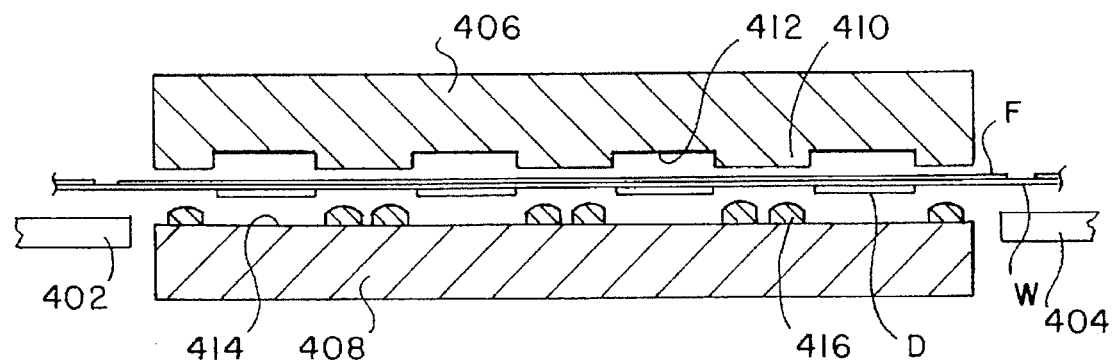
FIG. 9A is a schematic cross section of a die for forming a primary seal between the top foil sheet and web of bottom foil with the die shown in an open position at a sealing station in the frame assembly line.
Figure 9B:
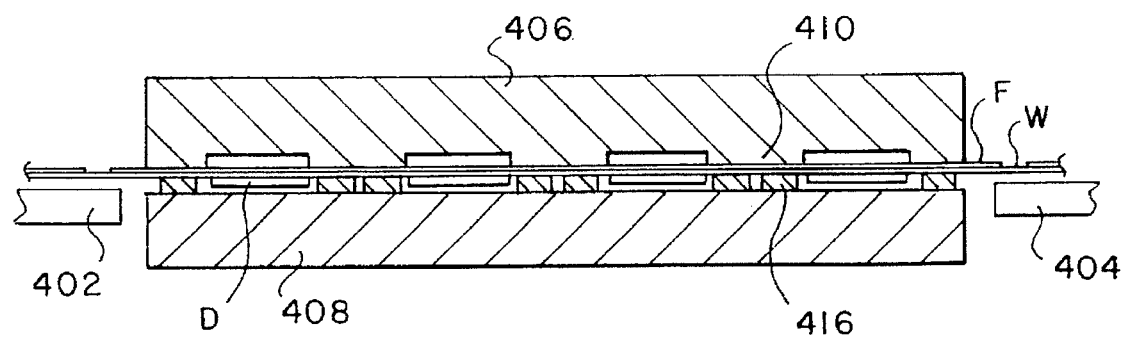
FIG. 9B is a schematic cross section similar to FIG. 9A with the die shown in a closed position.

Now referring to FIGS. 9A and 9B, a primary heat seal station is shown in schematic cross section and designated generally by reference 400. The web W moves along guides 402 and 404 at the upstream and downstream ends of the station 400. During the web advancement cycle, the web is moved into position with one sheet of top foil F registered between an upper die 406 and a lower die 408. The lower die 408 is supported in a stationary position by supports (not shown) secured to the manufacturing floor. The top die 406 is moveable in a short vertical stroke by a conventional press (not shown). The upper die 406 has a pattern of sealing fingers 410 separated by recessed regions 412. The cavities D in the web W are aligned with the recessed regions 412. The lower die 408 has a planar top surface 414 upon which are mounted hard rubber elements 416 which correspond in location to the fingers 410 in the upper die 406. The elements 416 preferably comprise #70 durometer hard silicone rubber available from Manville Rubber Co.

In operation, the sealing cycle begins after the web W has been moved to bring a single frame section into position in the station 400. Then, the upper die 406 is lowered forcibly against the web W to press the top foil sheet F against the underlying web of bottom foil at the positions corresponding to the fingers 410 and the rubber elements 416. The upper die 406 is heated to a temperature in the range from 190° C. to 202° C. with a preferred temperature being about 196° C. The dies 406 and 408 remain in the closed position as shown in FIG. 9B under a pressure of 60 ±5 bar for approximately 1.2 ±0.1 seconds, and then the dies are open to return to the position shown in FIG. 9A.

Figure 9C:
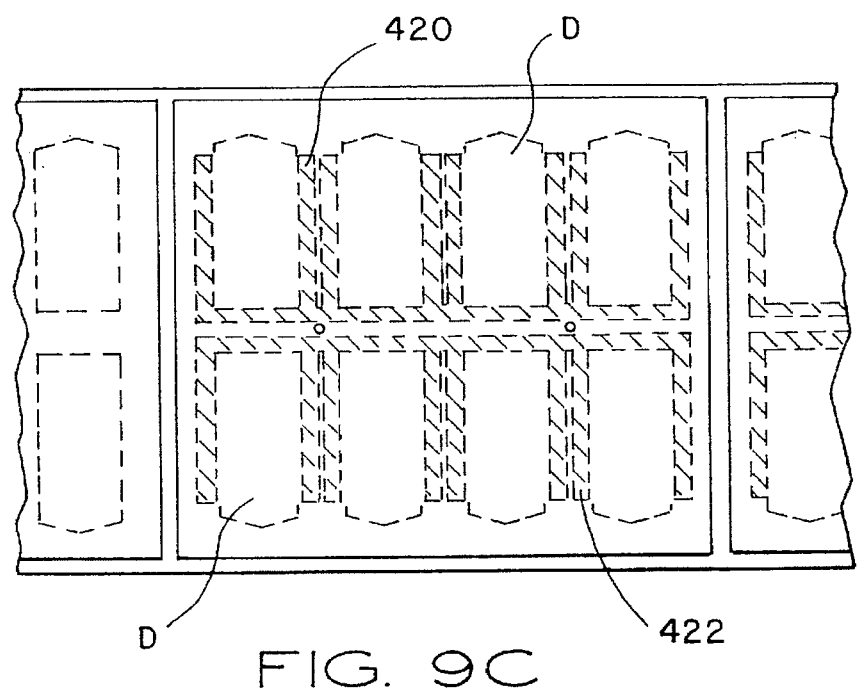
FIG. 9C is a top plan view illustrating the outline of a primary seal between a sheet of top foil and the underlying web of bottom foil, the seal being schematically depicted as cross-hatched areas in juxtaposition with the cavities in the bottom foil which are indicated in dashed outline.

Referring now to FIG. 9C, the result of the sealing operation just described is to fuse the polymer coatings on the facing surfaces of the web W and top sheet of foil F in a pattern indicated by the comb-shaped areas 420 and 422. These areas 420 and 422 define the primary seal pattern, which partially surrounds each cavity along its sides and interior end. The outer end of each cavity D remains unsealed so that gases can be introduced into the cavities in a conventional sterilization procedure.

After the primary seal has been formed at station 400, the web W travels through successive stations along the frame assembly line finally reaching a cutting station (not shown) where the web W is cut between adjacent sheets of top foil F to produce individual frames. The various stations through which the web travels in the frame assembly line are described more fully in the aforementioned copending application entitled "Apparatus for Feeding Foil Stock in a Process for Making Sealed Sterile Packages." After the individual frames are cut and the "good" frames separated from the rejected frames at the downstream end of the frame assembly line, the good frames are transported to a sterilization line, where sterilization of the suture products contained therein takes place.

At the end of the sterilization line (not shown) the individual frames are subjected to a secondary sealing operation while still in the sterile environment as will be described now with reference to FIG. 10. A single frame containing eight suture packets in corresponding cavities in two rows of four each is illustrated and designated generally by reference letter B. The various elements of the frame B are described more fully above with reference to FIG. 5.

Figure 10:
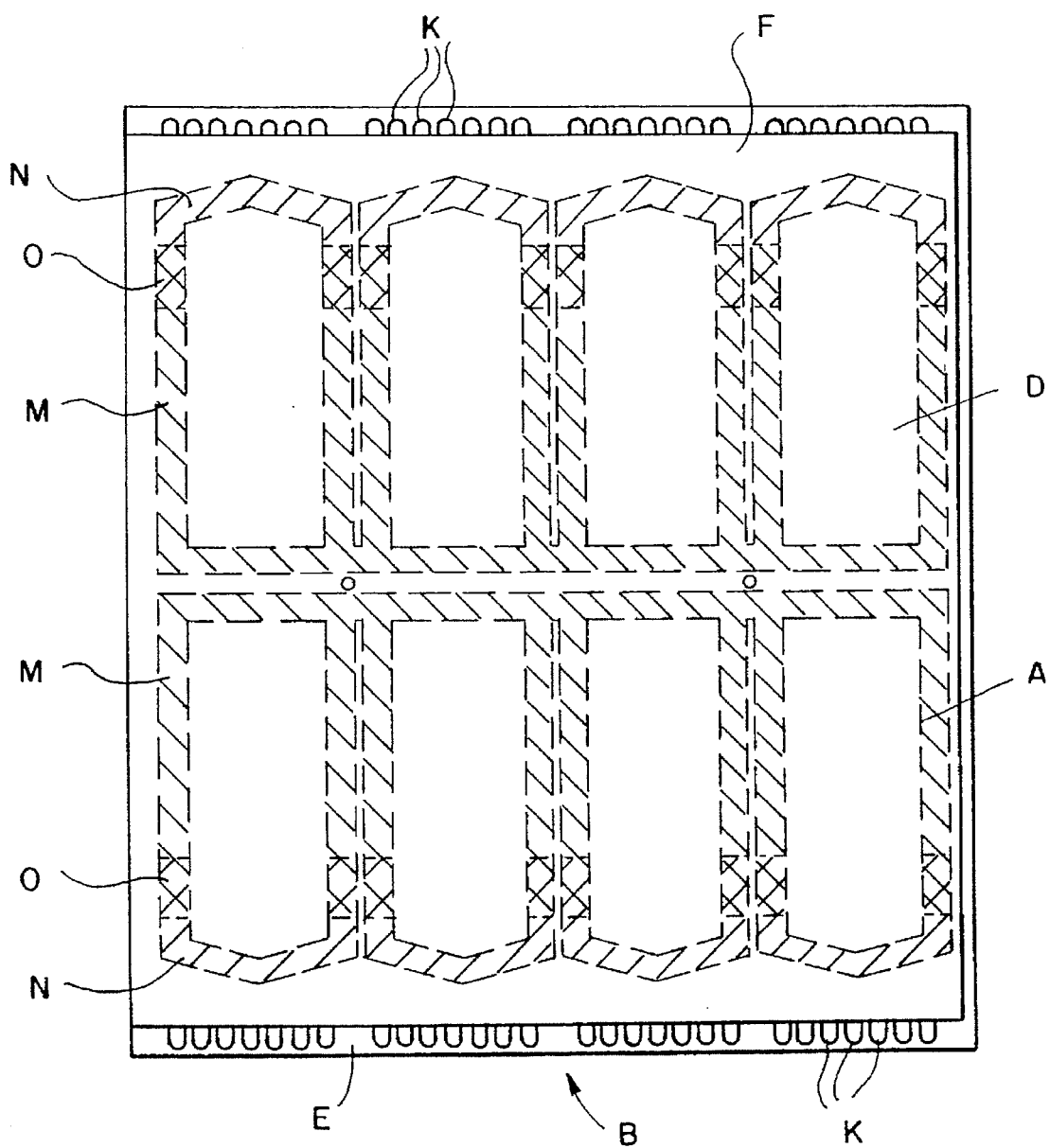
FIG. 10 is a top plan view similar to FIG. 9C of one frame of eight packages after passage through a sterilization line in which sterilization and secondary sealing procedures occur, a secondary seal being schematically depicted cross-hatched with the hatching diagonally opposite to the cross-hatching of the primary seal, such that the overlapping portions of both seals appear as double crosshatched areas.

In FIG. 10, the areas of the primary seal are cross-hatched diagonally in one direction and designated by reference letter M. The areas of the secondary seal are designated by reference letter N and are cross-hatched diagonally opposite to the cross-hatching of the primary seal M, such that the overlapping portions of both seals appear as double-cross-hatched areas designated by reference letter O.

The die mechanism for forming the secondary seal N operates in a manner similar to that used to form the primary seal M as described in connection with FIGS. 9A and 9B above. However, since the individual frames B are no longer carried by a continuous web, they must be loaded into and removed from the secondary sealing station at the end of the sterilization line by a different transport mechanism.

This is accomplished by feed line having a pair of conveyor belts (not shown) which support each individual frame in the area of the primary seal so that the belts can pass through the center of the sealing die mechanism without interfering with the sealing operation. The belts have cogs at spaced intervals to accommodate individual frames therebetween and advance them in a steady series of movements along the feed line. Between the belts and operable from below the feed line are locating pins which pass through the locating holes P (FIG. 5) of the frame B to precisely position each frame in the secondary sealing station. Guide rails (not shown) at the sides of the feed line center the frames so that the holes P will register with the locating pins. When the frame is in proper position, the belts pause in their cycle of movement and two sets of sealing dies (not shown) are closed down on opposite sides of the frame B to form the secondary seal patterns N as depicted in FIG. 10.

Now referring to FIG. 11A, the operation of a blanker-cartoner line will be described. Sterilized and completely sealed frames, each containing eight suture packets, are transported from the sterilization line stacked in magazines (not shown) to a frame unloading station 500. Individual frames are removed from stacks and placed on a feed line 550. As depicted in the enlarged view of FIG. 11B, the frames B move along the feed line 550 guided by side rails 552 and 554. A pair of belts 556 and 558 move along the feed line 550 to carry the frames B from station 500 to a blanking station 600. Spaced cogs 560 on the belts 556 and 558 maintain the frames in proper position. A series of pins 562 extend up from between the belts 556 and 558 and move in tandem therewith along the feed line 550. The pins 562 register with the locating holes P (FIG. 5) in each frame B to carry each frame into a precise position in the blanking station 600 where blanking dies (not shown) cut the frame to provide eight separate packages (such as the package A of FIG. 2) in a conventional blanking operation.

The individual packages are then carried on conveyor belts through a vision system station 650. The vision system inspects the individual packages for seal integrity and proper seal widths in a manner similar to that described in connection with the vision system of the copending application entitled "Apparatus for Feeding Foil Stock in a Process for Making Sealed Sterile Packages."

In order to provide for human inspection of the bottom surfaces of the packages, they are inverted on the conveyor belts at a flipper station 700, which is described more fully below. The conveyor belts then transport the individual packages through a human operator inspection station 750. The packages then arrive at a flopper station 800 where the packages are turned top-side-up in a manner described more fully below. The packages are then transported by parallel conveyor belts to a collating station 850 where they are arranged in stacks in preparation for cartoning. Finally, the stacks of packages are boxed in cartons at a cartoning station 900 using conventional equipment.

Now referring to FIG. 12A, the vision system and the operation of the flipper station 700 will be described. The packages A pass over a pair of cameras 652 and 654. The cameras each "look" at the bottom of a package in the area of the secondary seal N (FIG. 5). The vision system determines the width of the secondary seal N and the width of the cavity D in the overlap area O. If any such dimension is out of the specified range, the package is electronically "tagged" for rejection and removal from the line at the collating station 850 (FIG. 11). The vision system 650 can also determine whether foreign matter is in the secondary seal area N, and reject a package for lack of seal integrity.

As seen in FIG. 12A, as the packages pass beyond the cameras 652 and 654, they arrive on conveyor belts 702 and 704 in the flipper station 700. During a dwell phase of the movement cycle of the belts 702 and 704, flipper yokes 706 rotate the packages 180° and place them back on the belts. Two flipper mechanisms 708 and 710 are provided on opposite sides of the conveyor belts, each mechanism operating one set of four yokes.

Referring to FIG. 12B, each yoke 706 has two sets of upper and lower arms 712U and 712L, which may be moved from an open position to a closed position. The closed position is depicted in FIG. 12B. When the arms 712U and 712L are spaced apart in the open position, the packages can pass between the arms and come into positions for grasping by the yokes 706 as shown in FIG. 12A.

Now referring to FIG. 12C, the sequence of movements of the individual flipper yokes 706 will be described. An individual package A is moved into position and the arms 712U and 712L are brought together to grasp the edges of the package A in the seal area using robber pads 714. Then the yoke 706 is lifted vertically by slightly more than one-half the width of the package A as indicated by the LIFTING STEP. Then the yoke 706 is rotated 180° as depicted by the ROTATING STEP. Then the yoke 706 is lowered to return the inverted package A to the conveyor belt as depicted by the DROPPING STEP. Finally, the yoke arms 712U and 712L are separated from contact with the package A. Then the conveyor belt moves in the direction from left to right in FIG. 12A to bring an additional set of eight packages into the flipper station 700. In the next cycle, however, the individual flippers 706 rotate in the opposite direction but accomplish the same result. After the packages A have been rotated 180° and returned to the conveyor belts 702 and 704, they move into an inspection station 750 (FIG. 11) where human operators can visually inspect the bottom surfaces of each package.

Figure 12D:
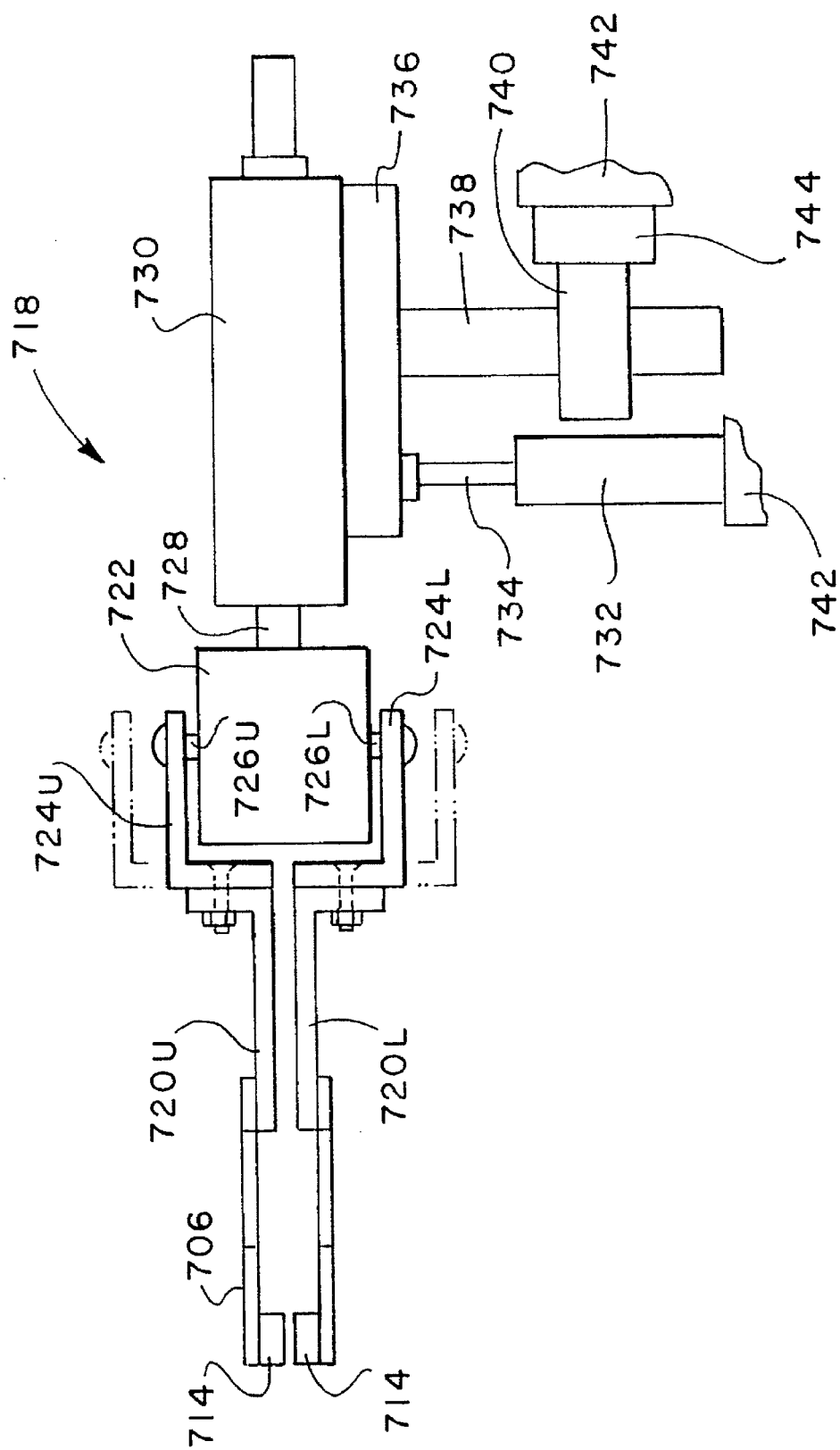
FIG. 12D is a schematic side view of one flipper yoke and the associated elements which control its movement.

Referring to FIG. 12D, a robot mechanism 718 for operating the yokes will be described. Each yoke pair has a respective common rod 720U and 720L, each such rod being connected to a pneumatic gripper 722 by respective L-shaped brackets 724U and 724L. The pneumatic gripper 722 extends and retracts piston rods 726U and 726L to open and close the yoke 706 to grasp and release the packages in a timed sequence of events. A shaft 728 is connected to the gripper 722 to rotate the gripper and yoke 706 in the above-described manner. The rotation of the shaft 728 is controlled by a pneumatic rotary actuator 730. A preferred robot mechanism 718 is the type RAM-5-180° rotary actuator with the SPL-5 gripper available from Zaytran, Inc. of Elyria, Ohio.

The entire robot mechanism 718 can be raised and lowered by an air cylinder 732. The air cylinder 732 raises the robot mechanism by forcing a piston rod 734 upward against a support plate 736 on which the rotary actuator 730 is mounted. The support plate 736 rides on a shaft 738, which is guided by a linear bearing 740. The bearing 740 is mounted to a stationary frame 742 by means of a bearing support 744. It will be appreciated that the robot mechanism 718 can be raised and lowered, and can cause the yoke 706 to open and close as well as to rotate 180° to perform the package flipping operation described above.

Figure 13A:
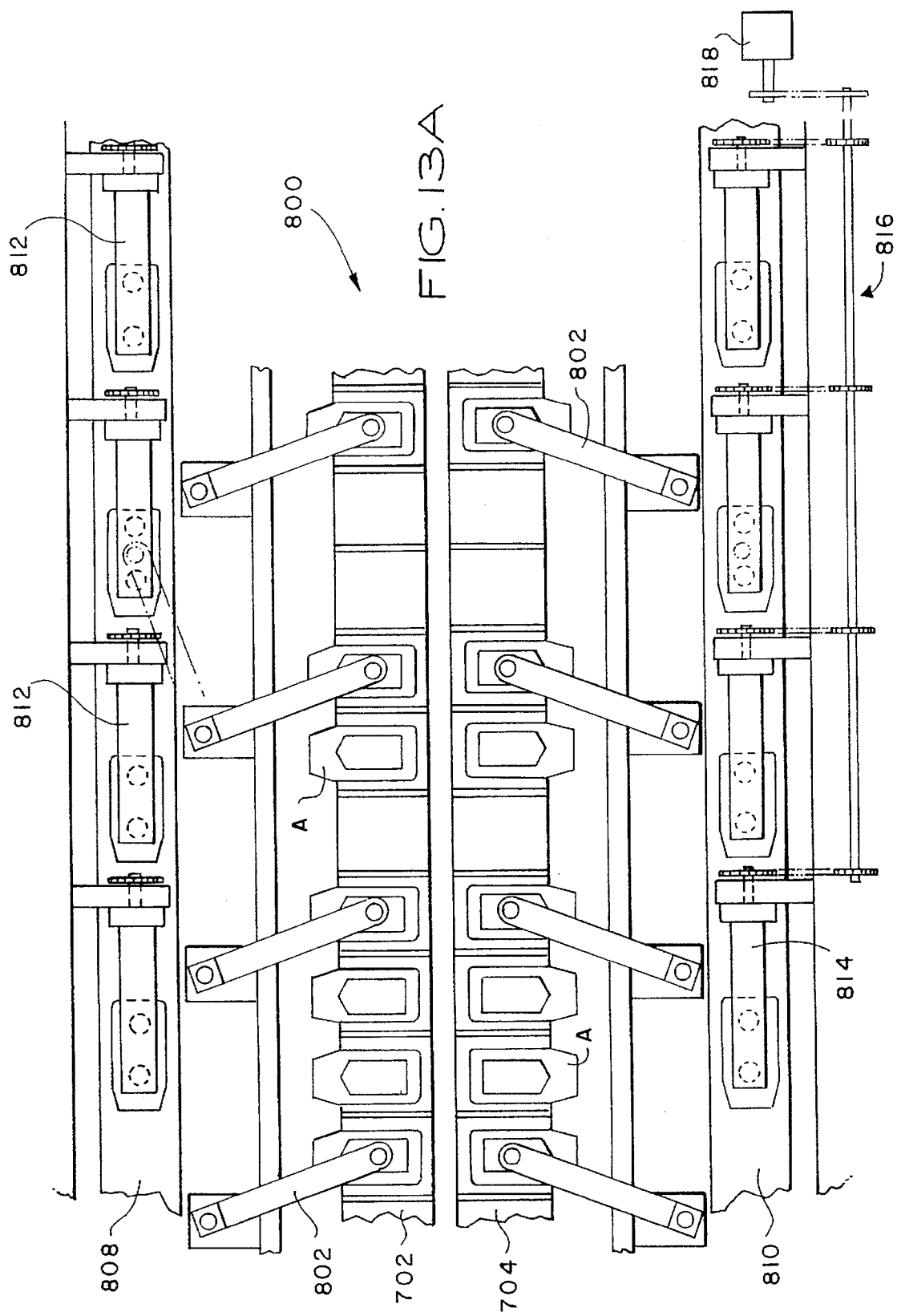
FIG. 13A is a schematic top view of a flopper station in the blanker-cartoner line showing synchronized mechanisms for first swinging the individual packages from inner conveyor belts to outer conveyor belts while reorienting the packages 90° with respect to their direction of travel down line, and then rotating them 180° with respect of their longitudinal axes to return them to a top-side-up position on the outer conveyor belts which move them to the next station.

Now referring to FIG. 13A, following visual inspection, the packages are transported by the conveyor belts 702 and 704 into a flopper station, designated generally by reference 800. A set of eight pivot arms 802 are provided at space locations along the conveyor belts 702 and 704, four pivot arms servicing belt 702 from one side and four other pivot arms servicing belt 704 from the other side of the line.

Figure 13B:
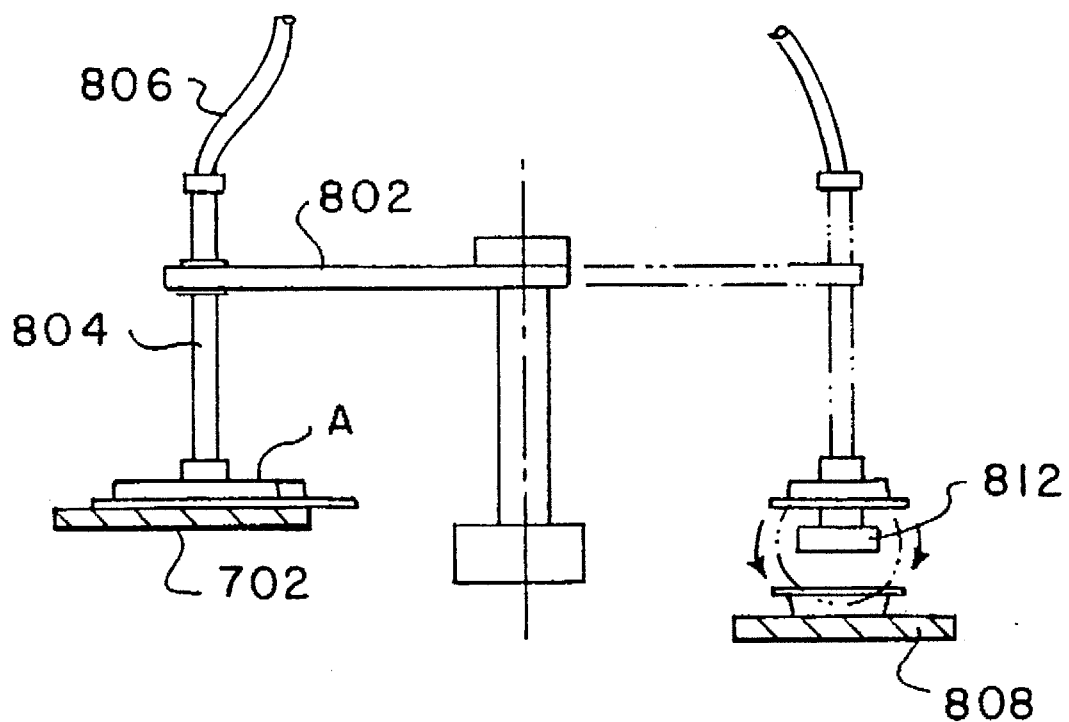
FIG. 13B is a schematic end view of one pivot arm and one flopper at the flopper station of the blanker-cartoner line.

Briefly referring to FIG. 13B, each pivot arm 802 includes a vacuum pickup head 804 connected by a hose 806 to a vacuum system (not shown). The pivot arm 802 picks up a package A and rotates it approximately 90° in position over a receiving belt 808. A second receiving belt 810 (FIG. 13A) on the opposite side of the line receives packages from the inner belt 704. The vacuum pickup 804 then releases the package A and places it on a flopper plate 812. Each of the flopper plates is connected to a vacuum system which holds the package in place momentarily until the package has been inverted and is ready to be dropped on to the receiving belt 808. Similar flopper plates 814 (FIG. 13A) are provided on the opposite side of the line.

Referring again to FIG. 13A, each flopper plate 812 and 814 is rotated 180° to invert a package by means of a system of gears and belts designated generally by reference numeral 816 (which for ease of illustration is shown fully only in connection with the belt 810). Each set of four flopper plates on opposite sides of the line are driven in a synchronized sequence of movements by an air actuated driver 818 (only one such driver being shown). It will be appreciated that the pivot arms 802 are spaced so that the individual packages A are picked up out of sequence and moved in a series of dwell phases from the inner belts 702 and 704 to the outer belts 808 and 810.

The procedure continues as described above in connection with FIG. 11A to stack the individual packages arriving via the belts 808 and 810 at a collating station, and then box the stacks of packages by a conventional cartoner mechanism at the final station of the blanker-cartoner line.

Although a preferred embodiment of the invention has been described herein with reference to the accompanying drawings, it will be appreciated that various alternatives and modifications thereof are within the spirit and scope of the invention as set forth in the appended claims.

We claim:

1. A method for making sterile suture packages, comprising:

a. feeding an elongated web of foil along a frame assembly line, the foil having a thin polymer coating on its top surface;

b. moving a frame section of the web into a cavity forming station having a die beneath the web;

c. during a pause in the web's movement, forcing air under pressure at the top surface of the web to deform the web into a plurality of large recesses to define cavities in the web and to deform the web into a plurality of small recesses located along the edges of the web to define rib-like depressions arranged in sets, each set corresponding to and lying adjacent to a cavity, and forcing a plug into each of the cavities from above the web to further define the shape of the cavities;

d. advancing the frame section to a suture packet loading station, and loading a suture packet into each cavity during a pause in the web's movement;

e. advancing the frame section to a top foil loading station, and loading a sheet of top foil atop the frame section during a pause in the web's movement, the sheet of top foil having a polymer coating on its bottom surface;

f. advancing the frame section to a sealing station and then, during a pause in the web's movement, exposing portions of the web and top foil partially around each cavity to heat and pressure to form a primary seal, leaving portions unsealed between each cavity and the adjacent corresponding set of rib-like depressions;

g. advancing the frame section to a cutting station, and then, during a pause in the web's movement, cutting the web at the leading and trailing edges of the frame section to provide a separate frame;

h. then, on a sterilization line, sterilizing the suture packets in the frame and then sealing portions of the frame at the outer periphery of each cavity to provide a complete peripheral heat seal around each cavity; and i. transporting the frame to a blanking station and separating a set of packages from the frame, each package having a single suture package contained therein in a sterile condition.

2. The method of claim 1 wherein the cavity forming station includes a stationary plenum above the web, and the die beneath the web is moved upwardly to clamp the web at the periphery of the plenum prior to forcing air under pressure into the plenum to deform the web, the plenum including a nozzle in its lower wall above each small recess in the die, each nozzle directing the pressurized air within the plenum against the web above each corresponding small recess in the die.

3. The method of claim 2 wherein the plugs pass through conforming openings in the lower wall of the plenum, each opening being slightly larger than the plug extending therethrough to provide a narrow passageway around the plug through which the pressurized air is directed at the web in the outline of the corresponding large recess in the die therebelow.

4. In a method for forming packages for surgical sutures, the steps comprising:

feeding a web of foil from a roll of foil stock into a framing machine, the web having a thin polymer coating on the upper surface thereof;

moving the web in a series of equally timed movements for processing at a series of discrete stations;

applying a die at a forming station to form a plurality of cavities in the web, and simultaneously forming rib-like depressions at the edges of the web, a set of such depressions corresponding to each cavity location;

loading suture packets into the cavities, one packet per cavity, each packet including a plastic tray in which a needle-suture assembly is retained;

placing a sheet of foil atop a section of the web to cover a predetermined number of cavities and packets therein, the top foil having a thin polymer coating on its bottom surface;

sealing selected portions of the top foil to the web around portions of the cavities by selectively applying heat to thermally fuse portions of the polymer coatings together, leaving the sides of the foil and web unsealed;

repeating the foregoing steps in sequence to bring a series of product sections to a cutting station; and cutting the web between each successive top foil sheet to form individual frames containing an array of cavities, each cavity containing a suture packet.

5. The method of claim 4 wherein each frame contains eight cavities arranged in an array of two rows of four cavities per row.

6. The method of claim 5 wherein the cavities are elongated and are disposed with their individual longitudinal axes transverse to the direction of travel the web, and wherein the rib-like depressions are elongated and parallel to the longitudinal axes of the cavities.

* * * * *